United States Patent [19]

Pless et al.

[11] Patent Number: 5,014,701
[45] Date of Patent: May 14, 1991

[54] IMPLANTABLE CARDIAC DEFIBRILLATOR EMPLOYING A DIGITAL WAVEFORM ANALYZER SYSTEM

[75] Inventors: Benjamin D. Pless, Menlo Park; Kenneth J. Carroll, San Jose, both of Calif.

[73] Assignee: Ventritex, Inc., Sunnyvale, Calif.

[21] Appl. No.: 354,138

[22] Filed: May 19, 1989

[51] Int. Cl.$^5$ .............................................. A61N 1/00
[52] U.S. Cl. ............................................... 128/419 PG
[58] Field of Search ......... 128/419 P, 419 D, 419 PG

[56] References Cited

U.S. PATENT DOCUMENTS

| 3,857,398 | 12/1974 | Rubin | 128/419 D |
| 4,184,493 | 1/1980 | Langer et al. | 128/419 D |
| 4,202,340 | 5/1980 | Langer et al. | 128/419 D |
| 4,340,062 | 7/1982 | Thompson et al. | 128/419 PG |
| 4,407,288 | 10/1983 | Langer et al. | 128/419 D |
| 4,515,159 | 5/1985 | McDonald et al. | 128/419 PG |
| 4,768,511 | 9/1988 | DeCote | 128/419 PG |
| 4,856,521 | 8/1989 | Irnich | 128/419 PG |

Primary Examiner—Francis Jaworski
Assistant Examiner—George Manuel
Attorney, Agent, or Firm—Gerstman & Ellis Ltd.

[57] ABSTRACT

An implantable medical device includes electrodes coupled to a patient's heart and sensing circuitry having inputs connected to the electrodes for sensing cardiac electrical signals. The sensing circuitry includes a digital waveform analyzer system which performs direct analysis of digitized ECG heart signals from the atrial and/or ventricular channels. This eliminates the need for the system microprocessor to perform direct analysis on raw ECG data. The benefit being that complex software algorithms are not required, saving microprocessor memory space. System current drain is also reduced since the microprocessor need not be active during every ECG sample.

9 Claims, 7 Drawing Sheets

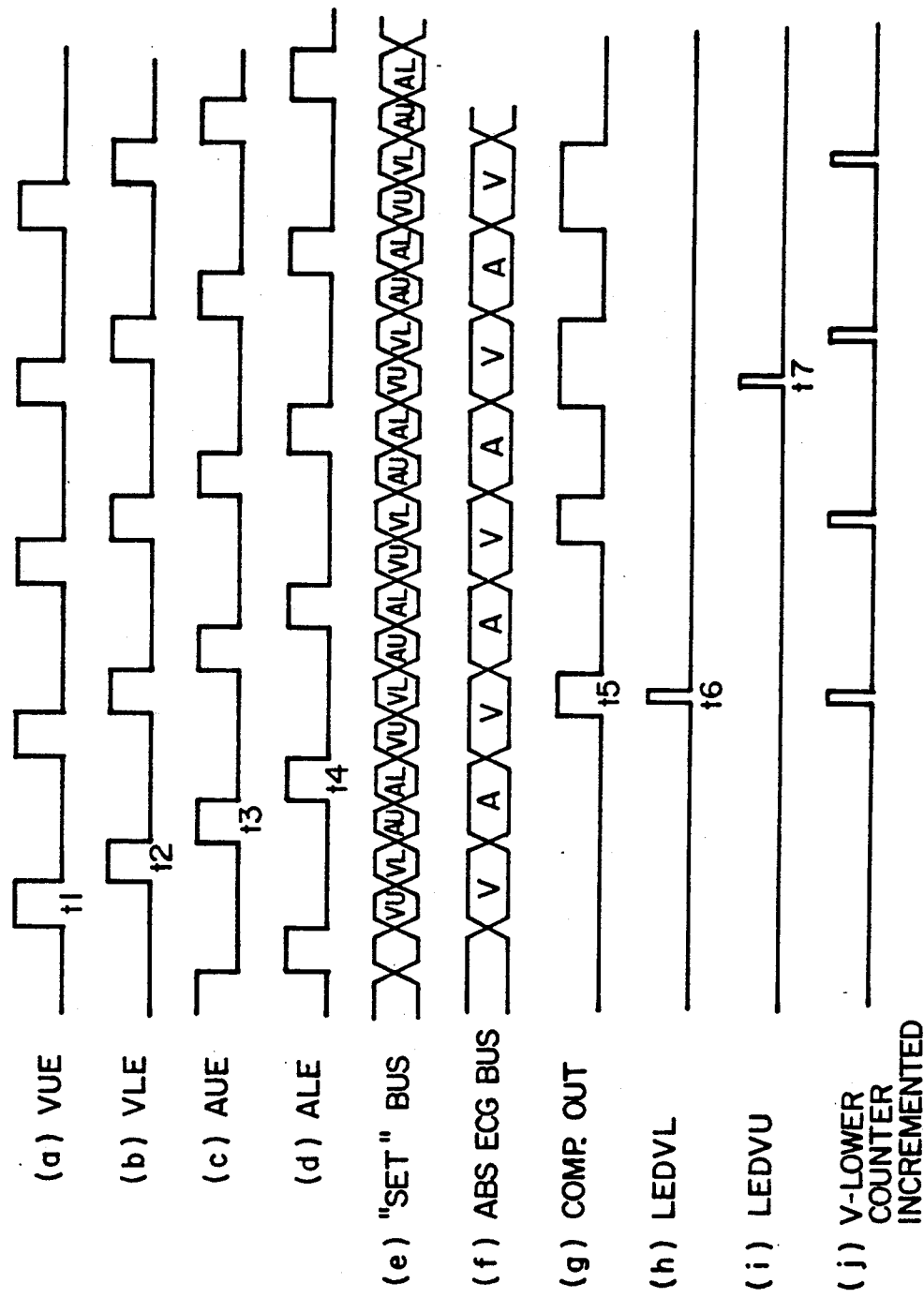

IMPLANTABLE CARDIAC DEFIBRILLATOR EMPLOYING A DIGITAL WAVEFORM ANALYZER SYSTEM

BACKGROUND OF THE INVENTION

This invention relates generally to implantable medical devices and more particularly, it relates to an implantable cardiac defibrillator employing a digital waveform analyzer system for performing direct analysis of digitized ECG heart signals from the atrial and/or ventricle heart chambers, thereby relieving much of the burden of the system microprocessor in performing data analysis.

In recent years, there has been substantial progress made in the research and development of defibrillating devices for providing an effective medical response to various disorders, such as ventricular fibrillation. Research effort has also been made toward developing improved sensing techniques for reliably monitoring heart activity so as to determine whether a defibrillating high energy shock is required.

There are known in the prior art electrical cardiac defibrillators which automatically detect and analyze the electrical activity of the heart and respond to certain predetermined parameters of the QRS complexes by electrically stimulating the heart so that abnormal heart beats can be corrected. Such a prior art cardiac defibrillator is disclosed in U.S. Pat. No. 3,857,398 to Leo Rubin, wherein a heart beat analyzer-control device is utilized to analyze automatically the QRS complexes of a heart beat and, when necessary, applies proper defibrillation or pacer pulses to the heart. However, the waveforms of the heart signals in this prior art cardiac defibrillator are essentially analyzed in an analog manner. The inventors of the present invention are unaware of an implantable cardiac defibrillator having a waveform analyzer system capable of performing signal conditioning and processing of digitized ECG heart signals so as to permit direct analysis of the same by a microprocessor.

It has therefore been determined that there is a need for an implantable cardiac defibrillator employing a digitized waveform analyzer system for extracting information from digitized ECG heart signals in an efficient and effective manner to better distinguish between malignant tachyarrhythmias, such as ventricular fibrillation and normal sinus rhythm.

SUMMARY OF THE INVENTION

It is a general object of the present invention to provide an implantable cardiac defibrillator employing a digital waveform analyzer system for extracting information from digitized ECG heart signals in an efficient and effective manner to better distinguish between malignant tachyarrhythmias and sinus rhythm.

It is another object of the present invention to provide an implantable cardiac defibrillator employing a digital waveform analyzer system for performing direct analysis of digitized ECG heart signals from the atrial and/or ventricular channels, thereby relieving much of the burden of the microprocessor in performing data analysis.

It is still another object of the present invention to provide an implantable cardiac defibrillator which includes a digital waveform analyzer system having means for generating interrupt signals when digitized ECG heart signals exceed programmed upper and lower thresholds.

It is still another object of the present invention to provide an implantable cardiac defibrillator which includes a digital waveform analyzer system having means for counting each subsequent sample of digitized ECG heart signals which is numerically greater than corresponding programmed threshold levels.

It is still yet another object of the present invention to provide an implantable cardiac defibrillator which includes a digital waveform analyzer system having means for counting the number of crossings of lower threshold levels and means for storing the most recent peak value of a digitized ECG heart signal.

In accordance with these aims and objectives, the present invention is concerned with the provision of an implantable medical device which includes electrodes and sensing circuitry. The electrodes are coupled to a patient's heart. The sensing circuitry is provided with inputs connected to the electrodes for sensing cardiac electrical signals. The sensing circuitry includes a digital waveform analyzer system for performing direct analysis of digitized ECG heart signals from the atrial and/or ventricular channels by a microprocessor.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein:

FIGS. 4(a)-4(j) are waveforms useful in understanding the operation of FIG. 3.

DESCRIPTION OF THE PREFERRED EMBODIMENT

Figure 1:
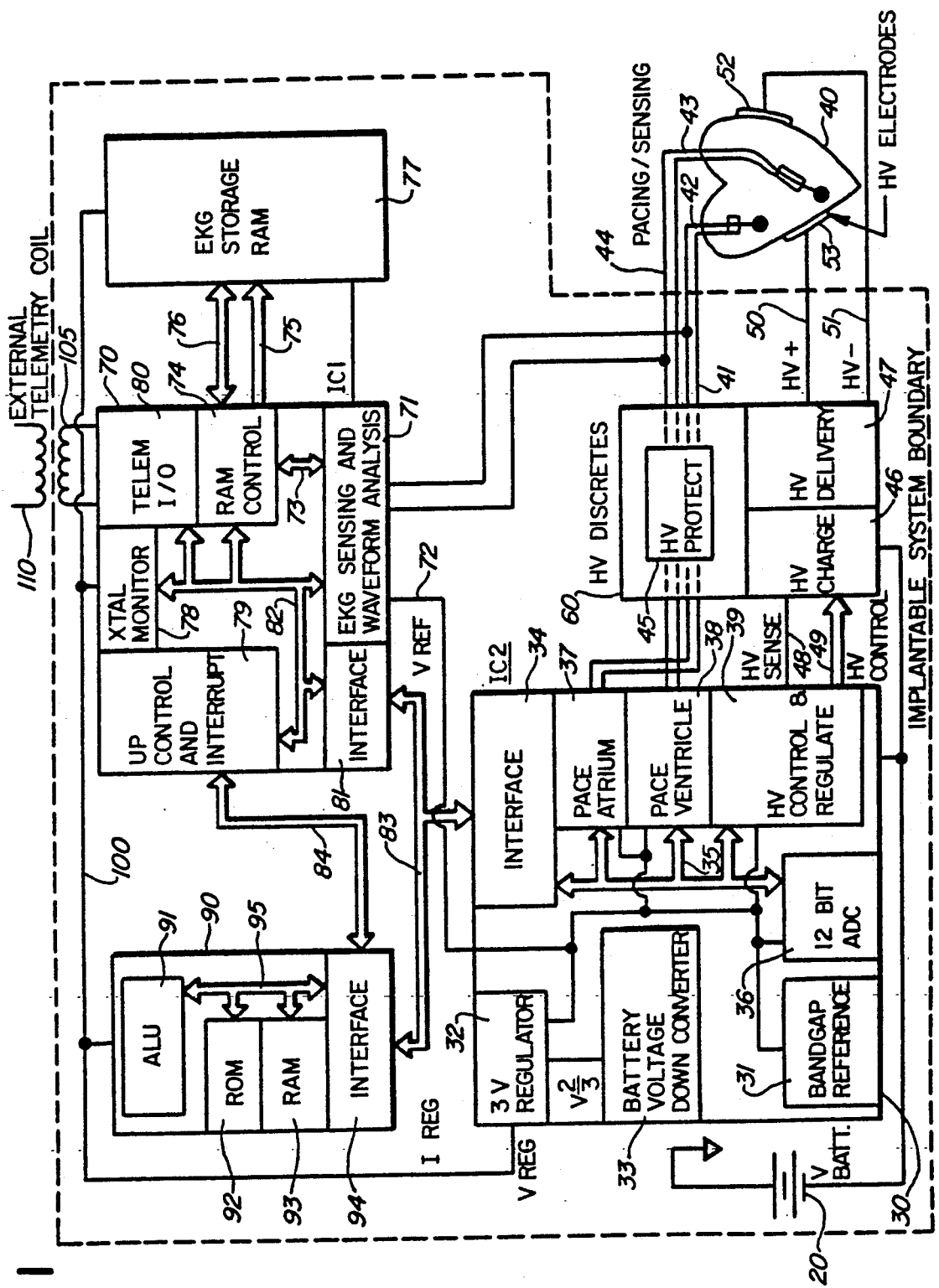
FIG. 1 is a block diagram of an implantable cardiac defibrillator, constructed in accordance with the principles of the present invention.

In FIG. 1, there is illustrated in a functional block diagram format the internal and external elements of an implantable cardiac defibrillator constructed in accordance with the principles of the present invention. A detailed description of the elements of FIG. 1 as well as their interconnection and operation has been presented in co-pending application Ser. No. 344,011, filed Apr. 26, 1989, entitled "Method For Cardiac Defibrillation" and assigned to the same assignee as the present invention, which is hereby incorporated by reference. Thus, the detailed description will not herein be repeated. However, a general description of the elements of FIG. 1 required for an understanding of the present invention will be presented.

In particular, FIG. 1 shows an implantable cardiac defibrillator which includes four integrated circuit chips IC1-IC4 and a set of high voltage discrete component blocks 45-47. The block 45 contains high voltage protection circuits which prevent the atrium and ventricle pacing circuits 37 and 38 from being damaged by the defibrillation voltage. The block 46 is a high voltage charge block and contains a high voltage capacitor that is charged to deliver a defibrillating pulse. The defibrillating pulse is delivered from the high voltage delivery block 47 to electrodes 52 and 53 connected to the heart 40 via lines 50 and 51.

The chip IC1 contains an ECG sensing and waveform analysis block 71 which receives ECG heart signals to be monitored and processed. Specifically, the heart signals coming from the atrium are fed to the sensing and waveform analysis block 71 via the line 42. The heart signals coming from the ventricle are fed to the block 71 via the line 44.

The block 71 includes a first three-stage amplifier/filter network for sensing the analog heart signals in the atrium and a second three-stage amplifier/filter network for sensing the analog heart signals in the ventricle. The block 71 includes a waveform digitization network which receives the analog output signals from either the first network or the second network via an analog multiplexer. The waveform digitization network converts the analog ECG heart signals from the atrium and/or ventricle into a six-bit plus sign digitized signal plus a channel identifier bit.

The block 71 further includes a digital waveform analyzer system which accepts the digitized ECG heart signals in the six-bit plus sign format with the channel identifier bit that denotes the atrial channel or ventricular channel. The waveform analyzer system 10 is utilized for performing signal conditioning and processing of the digitized ECG heart signals so as to permit direct analysis of the same by the microprocessor IC3 (FIG. 1). In particular, the waveform analyzer system functions to send out interrupt signals if the digitized ECG heart signals exceed certain programmed threshold levels and to provide stored ECG values upon demand.

Figure 2:
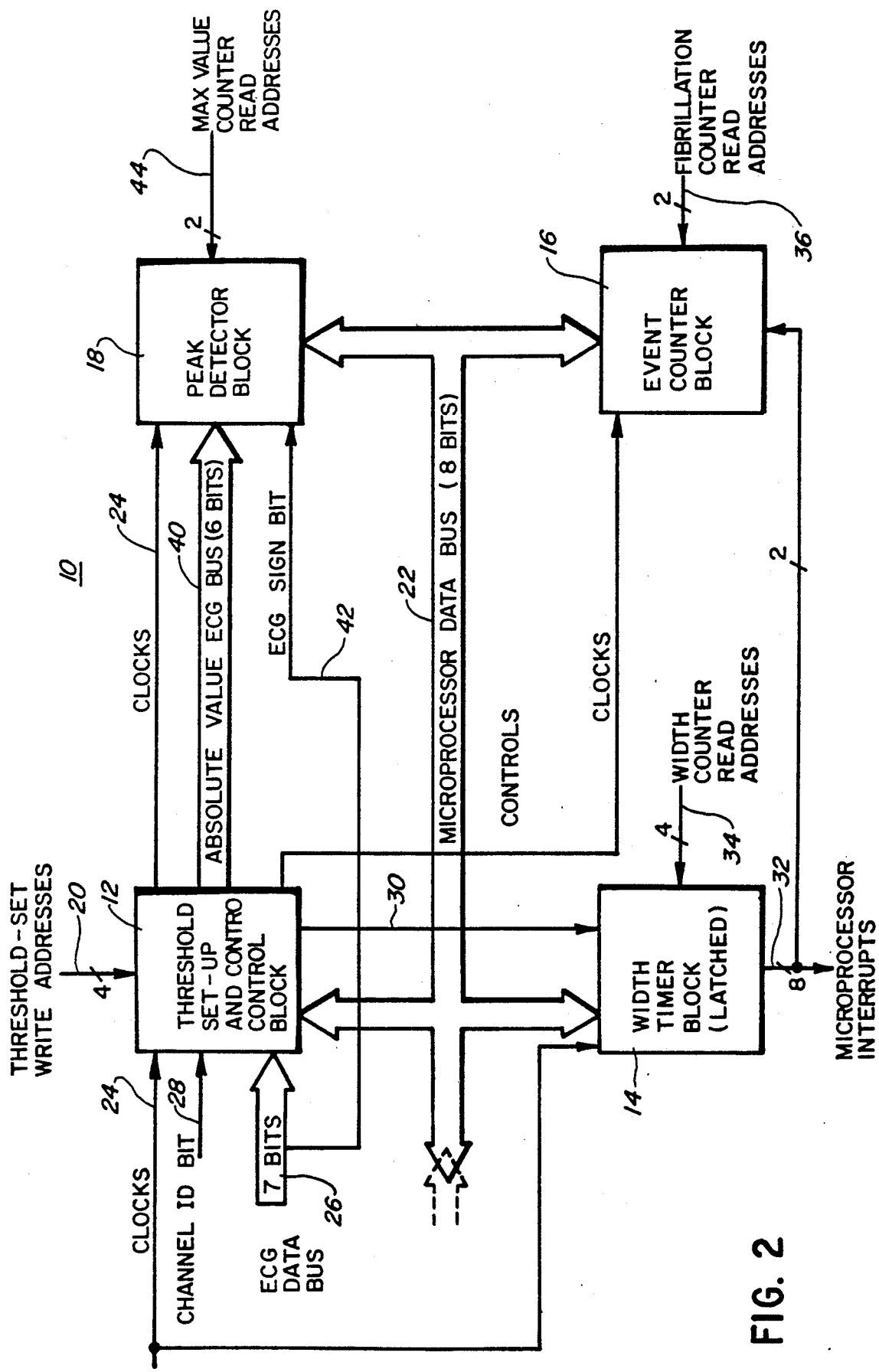
FIG. 2 is a simplified block diagram of a digitized waveform analyzer system, constructed in accordance with the principles of the present invention.

In FIG. 2, there is illustrated in a simplified block diagram form a digitized waveform analyzer system 10 constructed in accordance with the principles of the present invention. The waveform analyzer system 10 is comprised of a threshold set-up and control block 12, a width timer or counter block 14, an event counter block 16, and a peak detector block 18. The threshold and control block 12 is programmed with four amplitude threshold levels via threshold-set write addresses ADRVUTHRW, ADRVLTHRW, ADRAUTHRW, and ADRALTHRW on 4-bit bus 20, which correspond to a ventricular upper level "VU", a ventricular lower level "VL", an atrial upper level "AU", and an atrial lower level "AL". Generally, the upper threshold levels will be made to be of a higher numerical value than the respective lower threshold levels. Further, the thresholds for the atrium and the ventricle are typically set to different levels. Each of the four thresholds consists of a six-bit word which are loaded from the 8-bit microprocessor data bus 22 of which the sixth and seventh bits are "don't cares."

The threshold and control block 12 receives also a clock input on line 24, 7-bit (six-bit plus sign) input signals corresponding to digitized ECG heart signals on the bus 26, and a channel identifier bit on line 28. The threshold and control block 12 rectifies the input signals on the bus 26 and compares it against each of the four programmed six-bit threshold levels. The rectification permits the comparison of the input signals of both polarities with a single threshold level rather than requiring the need of one positive threshold value and another negative value threshold. Enable control signals within the block 12 insure that the appropriate threshold is compared to the 2 channel digitized ECG input signal in a correct time sequence. Once a threshold level has been exceeded or crossed, corresponding interrupt signals LEDVU, LEDVL, LEDAU and LEDAL are generated when appropriate on bus 32 via the width timer block 14. For example, the interrupt signal LEDVU refers to the crossing of the ventricular upper level by the "leading edge" of the digitized ECG input signal. In other words, there is a crossing of the upper threshold in a positive or numerically increasing direction.

The width timer block 14 receives the enable control signals on the bus line 30 and the clock input on the line 24. The block 14 includes four 8-bit "width" counters which are associated with the threshold levels. After a particular threshold level has been exceeded, the associated width counter is incremented for each subsequent sample of the input signal which is numerically greater than that threshold. The associated width counter stops counting when the same threshold is crossed in the downwardly-going direction. At this time, corresponding interrupt signals TEDVU, TEDUL, TEDAU and TEDAL are also generated when appropriate on the bus 32. For example, the interrupt signal TEDVU refers to the ventricular upper level being crossed by the "trailing edge" of the heart complex represented by the digitized ECG input signal. The values of the width counters can be read by the microprocessor via the bus 22 when addressed on bus 34 by address signals ADRVURD, ADRVLRD, ADRAURD and ADALRD. The maximum count is 255 samples (2 ms per sample) at which point the width counters are locked out. The width counters are then readable and are cleared upon an "upwardly-going" threshold crossing.

The event counter block 16 is comprised of four counters, a first pair of counters for the atrial channel and a second pair of counters for the ventricular channel. One of the counters in the first pair is incremented for a crossing of the ventricular lower threshold level with the sign bit of the ECG data signal set to "one." The other one of the counters in the first pair is incremented for a crossing of the ventricular lower threshold level with the sign bit of the ECG data signal set equal to "zero." Similarly, one of the counters of the second pair is incremented for a crossing of the atrial lower threshold level with the sign bit of the ECG data signal set equal to "one." The other one of the counters in the second pair is incremented for a crossing of the atrial lower threshold level with the sign bit of the ECG data signal set equal to "zero." Thus, the sign bit is used to determine whether the "plus" or "minus" counter is to be incremented, which is an indication of the polarity of the biphasic waveform.

The event counter block 16 receives as inputs the interrupt signals LEDVL and LEDAL from the width timer block 14 so that the appropriate counter is incremented each time the interrupt signals are generated. Each of the four counters is a 4-bit counter and thus can count up to "fifteen." Then, the counter is locked out so as to prevent a rolling over to the initial position. The values of the event counters can be read by the microprocessor on the bus 22 when addressed on the bus 36 by address signals ADRFIBVRD and ADRFIBARD. The counters are "cleared when read" and appear on the bus 22 in pairs, e.g., an 8-bit word.

The peak detector block 18 is comprised of two 7-bit latches, a first latch for the atrial channel and a second latch for the ventricular channel. The latches are utilized for storing the most recent peak values of the ECG data signal. The peak detector block 18 receives as inputs the clock signal on the line 24, the rectified (absolute) value of the ECG data signal from the threshold and control block 12 via bus 40, the sign bit of the ECG data signal via line 42, and the interrupt signals LEDVU and LEDAU. The stored peak value may be a positive waveform or a negative waveform. Further, only the last peak is the one that remains. The interrupt signals are used to reset or clear the respective latches upon an upward crossing of the corresponding atrial upper level threshold level and ventricular upper threshold level. The values of the latches can be read by the microprocessor on the bus 22 when addressed on bus 44 by address signals ADRVMAXRD and ADRAMAXRD. The latches are also "cleared when read" and appear on the bus 22 as six-bits in rectified form plus the appropriate sign bit.

Figure 3A:
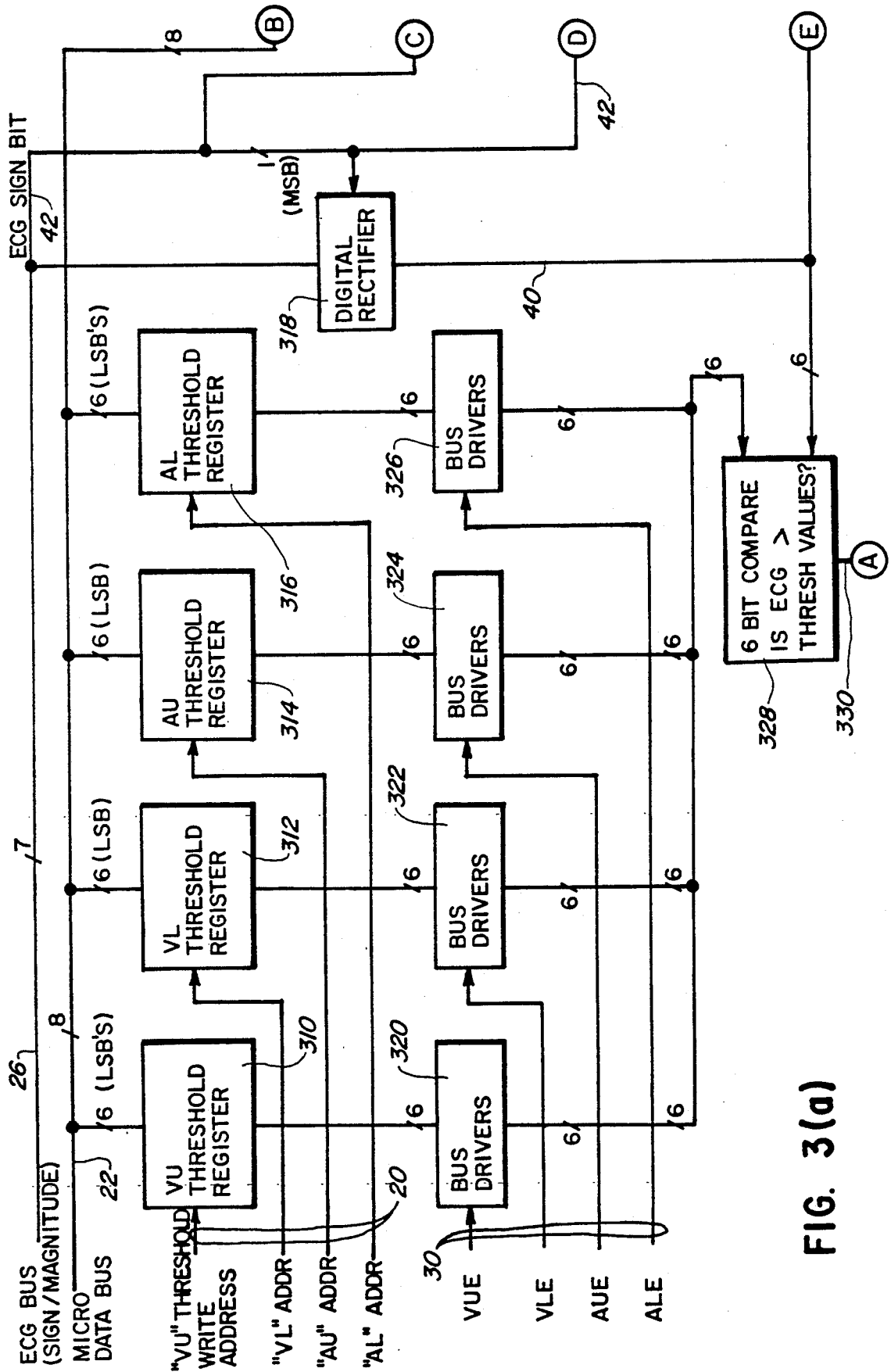
FIGS. 3(a)-3(d), when connected together, is a detailed block diagram of circuitry suitable for use in the various blocks shown in FIG. 2.

FIGS. 3(a)-3(d), when connected together, shows in a more detailed block diagram form suitable circuitry for use in the blocks 12, 14, 16 and 18 of FIG. 2. Like reference numerals have been employed throughout FIG. 3(a)-FIG. 3(d) to designate the like parts. In FIG. 3(a), the four threshold registers 310, 312, 314 and 316 in the block 12 are used to store the corresponding ventricular upper threshold level "VU", ventricular lower threshold level "VL", atrial upper threshold level "AU", and atrial lower threshold level "AL" from the microprocessor data bus 22 when addressed by the address signals ADRVUTHRW, ADRVLTHRW, ADRAUTHRW, and ADRALTHRW on the bus 20. The ECG data signal on the bus 26 is rectified by the digital rectifier 318. When the corresponding bus drivers 320, 322, 324 and 326, coupled to the outputs of the respective registers 310-316, are enabled by the control signals VUE, VLE, AUE and ALE the appropriate threshold level is sent to one input of the comparator 328. The other input of the comparator 328 is from the output of the digital rectifier 318. The output of the comparator 328 on line 330 is sent to the width timer block 14.

Figure 3B:
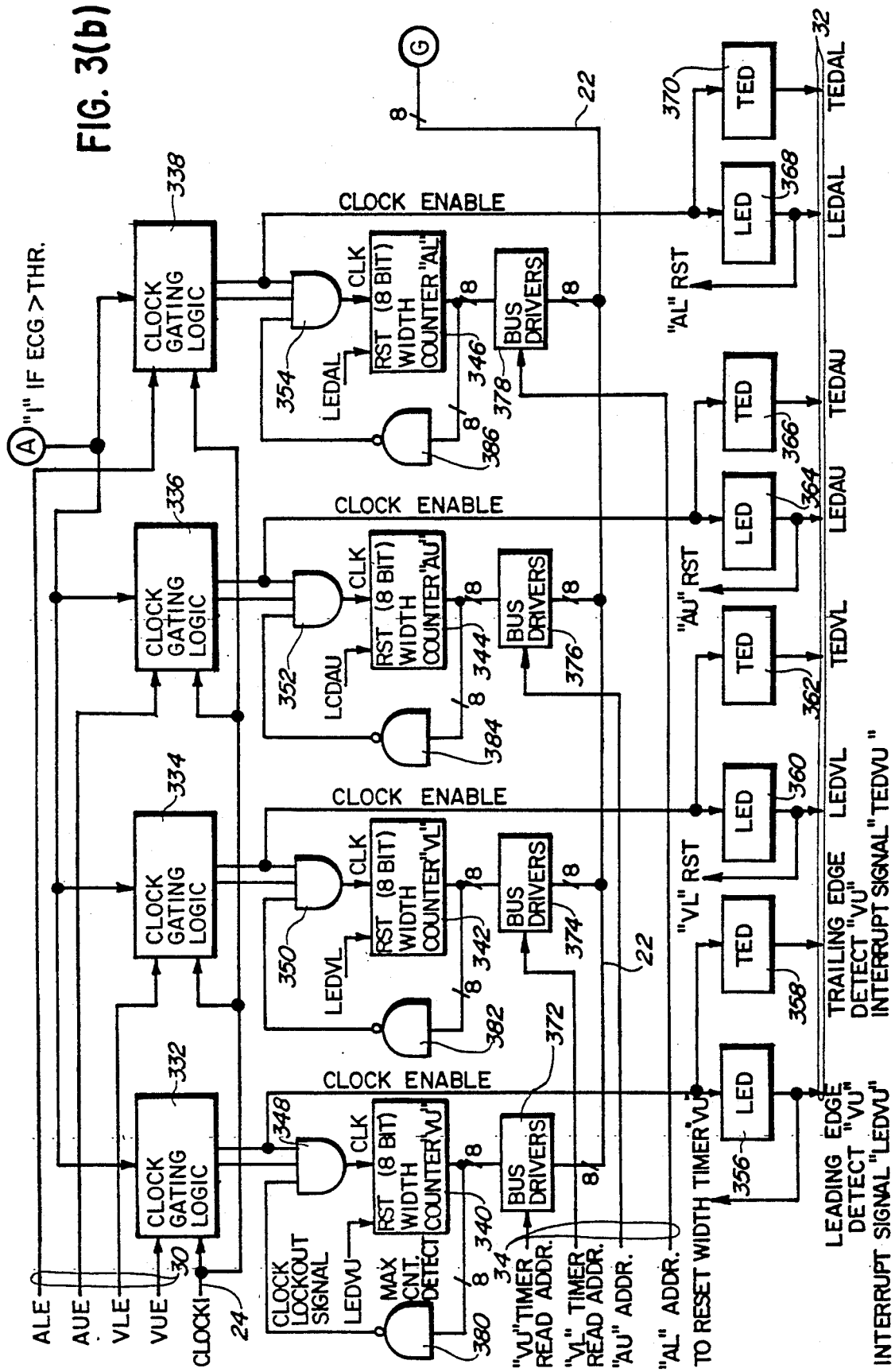

In FIG. 3(b), there is shown four clock gating logic circuits 332, 334, 336 and 338 coupled to receive as an input the line 330 from the comparator 328 in the block 12. The logic circuits 332-338 also receive as inputs the clock input on the line 24 and the control signals VUE, VLE, AUE and ALE on the bus line 30. The logic circuits are used to pass the appropriate output of the comparator 328 to the corresponding 8-bit width counters 340, 342, 344 and 346 via respective AND logic gates 348, 350, 352 and 354. The logic circuits 332-338 are also used to generate the eight interrupt signals LEDVU, TEDVU, LEDVL, TEDVL, LEDAU, TEDAU, LEDAL and TEDAL on the bus 32 via respective edge detectors 356, 358, 360, 362, 364, 366, 368 and 370. When the corresponding bus drivers 372, 374, 376 and 378, coupled to the outputs of the respective width counters 340-346 are addressed by the address signals ADRVURD, ADRVLRD, ADRAURD and ADRALRD on the bus line 34, the microprocessor reads the values of the associated width counter via the bus 22. The output of each of the width timers is also fed back to the respective one of the AND logic gates 348-354 via NAND logic gates 380, 382, 384 and 386 for preventing a rollover count from the maximum value.

Figure 3C:
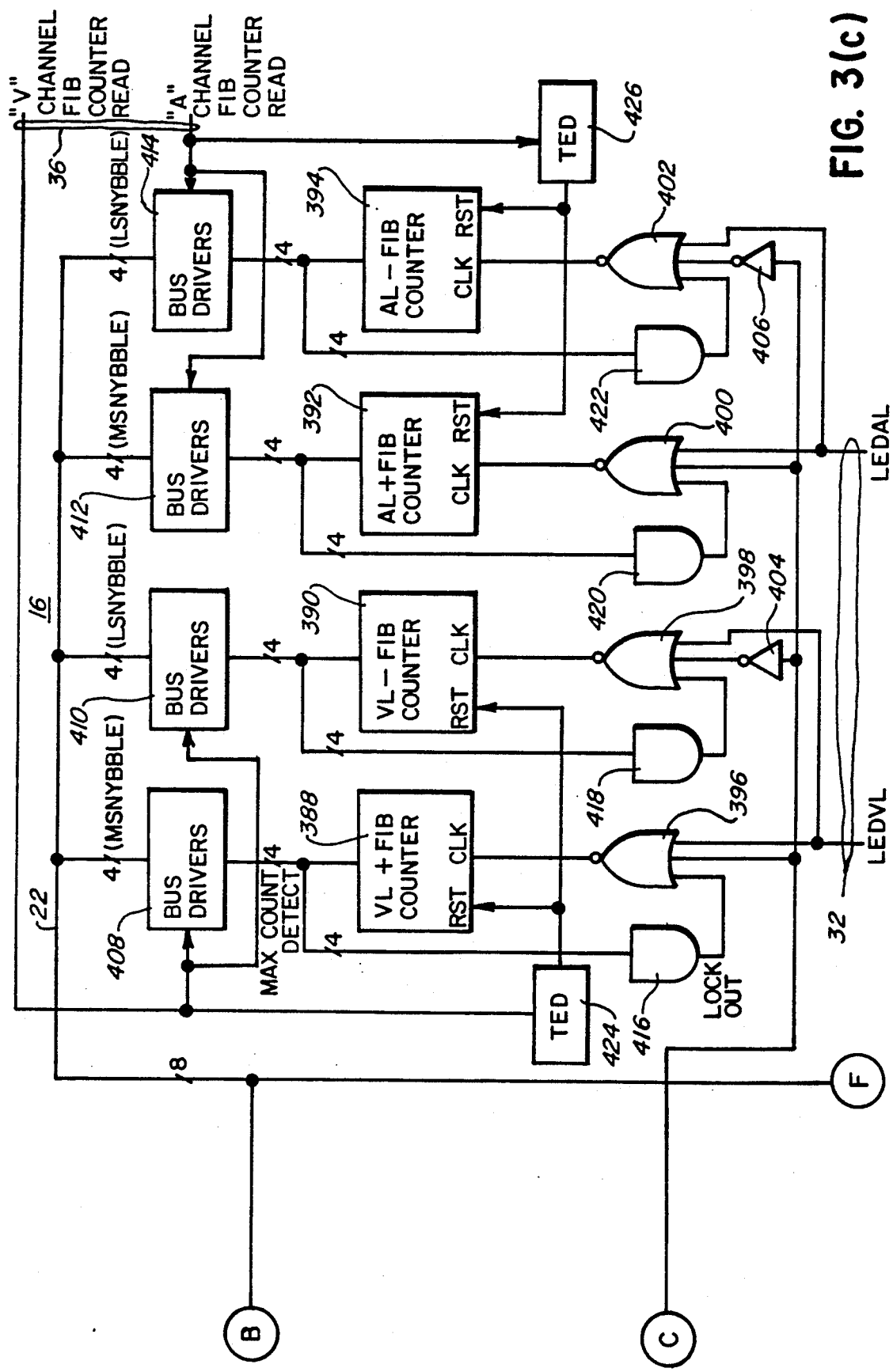

In FIG. 3(c), there is illustrated the "plus" and "minus" event (fibrillation) counters 388, 390 for the ventricular channel and the "plus" and "minus" event (fi-brillation) counters 392, 394 for the atrial channel in the event counter block 16. The fibrillation counters 388-394 receive inputs via corresponding NOR logic gates 396, 398, 400 and 402. The sign bit signal on the line 42 is inverted by inverters 404, 406 before being fed to an input of the NOR gates 398 and 402. Thus, the polarity of the ECG sign bit determines the counter to be incremented. A crossing at the lower ECG thresholds cause either LEDVL or LEDAL to pulse. It is these signals which increment the respective fibrillation counters. When the bus drivers 408, 410, 412 and 414, coupled to the output of the respective fibrillation counters 388-394, are addressed by the address signals ADRFIBVRD and ADRFIBARD on the bus line 36, the microprocessor reads the values of the counters 388-394 via the bus 22. The outputs of each fibrillation counter is also fed back to the NOR gates via respective AND logic gates 416, 418, 420 and 422 to lock out the counters when it has reached its maximum count. A trailing edge detector 424 is used to reset the counter 388 and 390, and a detector 426 is used to reset the counters 392 and 394 on the falling edge of the address strobes ADRFIBVRD and ADRFIBARD. The fibrillation counters are, therefore, cleared when read.

Figure 3D:
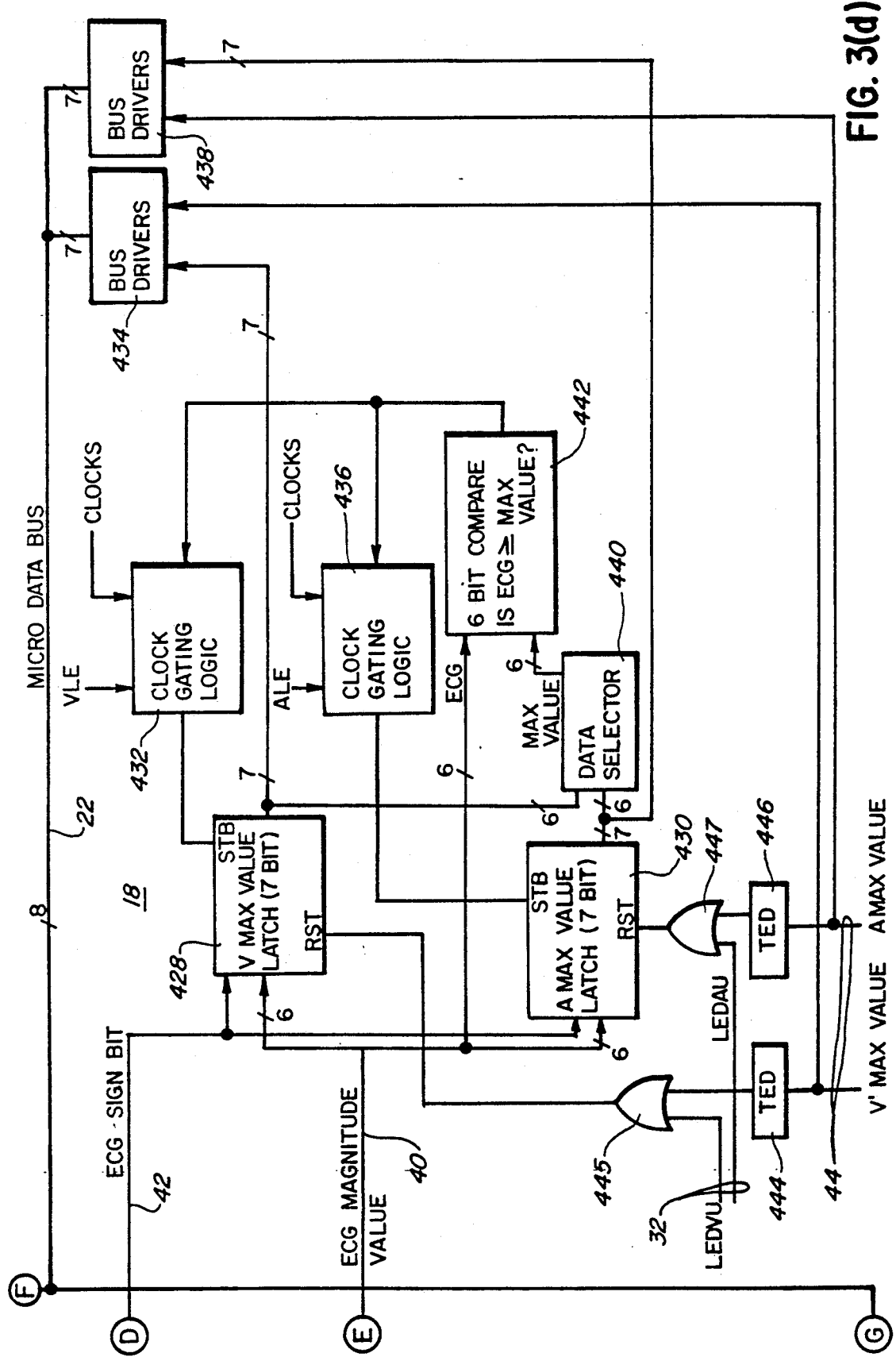

In FIG. 3(d) there is depicted in the peak value detector block 18 a latch 428 for storing the maximum value of the ECG data signal plus bit corresponding to the ventricular channel and a latch 430 for storing the maximum value of the ECG data signal plus bit corresponding to the atrial channel. The latch 428 receives as an input signal the ECG magnitude value on the line 40 and the ECG sign bit on the line 42. The data selector 440 applies either the current value of the latch 428 or the latch 430 onto the comparator 442. This is synchronized to occur such that the value on the ECG data bus is appropriate to the ventricular or atrial channel. If the comparator 442 determines that the value on the ECG bus is greater than the current value in the respective latch 428 or 430 then the value stored in that latch is changed to be the value currently on the ECG bus 40. If the comparator 442 determines that the current value in the latch 428 or 430 is not exceeded by the value on the ECG bus 40 then the latch value is not changed. The control signal VLE is applied to the control gate logic 432 whose output is fed to the latch 428. The output signal from the gating logic 432 is used to store into the latch 428 the value on the ECG bus 40. Similarly, the control signal ALE is applied to the clock gating logic 436 whose output is fed to the latch 430. The signal from the gating logic 436 is used to store into the latch 430 the value on the ECG bus 40.

When the bus drivers 434 and 438 are addressed by the address signals ADRVMAXRD and ADRAMAXRD on the bus 44, the outputs of the respective latches are sent to the microprocessor data bus 22. An edge detector 444 is used to reset the latch 428 on the trailing edge of the address ADRVMAXRD via OR logic gate 445. The latch 428 is thus cleared when read. An edge detector 446 is used to reset the latch 430 on the trailing edge of address ADRAMAXRD via OR logic gate 447. The latch 430 is thus cleared when read. The latches 428 and 430 are also resettable by the interrupt signals LEDVU and LEDAU on the bus 32.

It should be clearly understood that the block diagrams of FIGS. 3(a)-3(d) and the descriptions thereof are primarily functional in nature and that numerous variations and modifications of the blocks thereof are possible so as to achieve the same desired result. Further, some functions related to the overall operation of the cardiac defibrillator, not particularly relevant to an understanding of the operating principles of the present invention, have not been included in FIGS. 3(a)-3(d).

The operation of the circuitry of the waveform analyzer system shown in FIGS. 3(a)-3(d) will now be explained with reference to the waveform diagrams of FIGS. 4(a)-4(j). The enable control signals VUE, VLE, AUE and ALE shown in FIGS. 4(a)-4(d) are used to sequentially send the outputs of the registers 310-316 to one of the inputs of the comparator 328 between the times t1-t4. FIG. 4(e) shows the threshold values from the threshold registers and the manner in which they are applied to the comparator. The rectified ECG data signal from the digital rectifier 318 is shown in FIG. 4(f). The comparator 328 sequentially compares the outputs from the registers 310-316 with the rectified ECG data signal and generates an output shown in FIG. 4(g). At the time t5, the output of the comparator indicates that the value of the ECG data signal is greater than the programmed or set threshold value.

In FIG. 4(h), the interrupt signal LEDVL at the time t6 indicates that the ventricular lower threshold level has been crossed in the upwardly-going direction by the ECG data signal. This interrupt signal LEDVL is also used to either increment the fibrillation counter 388 if the ECG sign bit is "zero" or to increment the fibrillation counter 390 if the ECG sign bit is "one." In FIG. 4(i), the interrupt signal LEDVU at the time t7 indicates that the ventricular upper threshold has been crossed in the upwardly-going direction by the leading edge of the ECG data signal. The pulses in FIG. 4(j) represent the output of the AND logic gate 350 (FIG. 3(b)), which is used to increment the width counter 342 until there is a crossing of the ventricular lower threshold level in the downwardly-going direction by the ECG data signal (not shown).

From the foregoing detailed description, it can thus be seen that the present invention provides an implantable medical device which employs a digital waveform analyzer system for performing direct analysis of digitized ECG heart signals from the atrium and/or ventricle channels by a microprocessor. The waveform analyzer system is formed of a threshold and control block, width timer block, event counter block and peak detector block for performing signal conditioning and processing of the digitized ECG heart signals.

The waveform analyzer provides information such as the most recent peak amplitude of a heart complex and the number of time samples of a heart complex above a lower and upper threshold. From this information, the microprocessor can simply determine the complex width, complex height and complex leading and trailing edge slopes without having to analyze raw ECG data, which would be wasteful of memory capacity.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. An implantable medical device comprising:
   electrode means adapted to be coupled to a patient's heart;
   sensing means having an input connected to said electrode means for sensing analog ECG heart signals;
   analog-to-digital means for converting the analog ECG heart signal into a digitized ECG heart signal; and
   waveform analyzer means responsive to said analog-to-digital converter means for performing signal conditioning and processing of the digitized ECG heart signal; and means for providing signals from said waveform analyzer means to a microprocessor.

2. An implantable medical device as claimed in claim 1, wherein said waveform analyzer means comprises threshold means for generating interrupt signals when the digitized ECG heart signal exceeds programmed upper and lower threshold levels.

3. An implantable medical device as claimed in claim 2, wherein said waveform analyzer means further comprises width timer means responsive to said interrupt signals for counting each subsequent ECG heart signal which is greater than said programmed threshold levels.

4. An implantable medical device as claimed in claim 2, wherein said waveform analyzer means further comprises event counter means responsive to said interrupt signals for counting each crossing of the lower threshold levels when a sign bit of the ECG heart signal has a first value and for counting each crossing of the lower threshold levels when the sign bit has a second value.

5. An implantable medical device as claimed in claim 2, wherein said waveform analyzer means further comprises peak detector means for storing a most recent value of the ECG heart signal.

6. An implantable medical device as claimed in claim 2, wherein one of said upper threshold levels corresponds to the ventricular channel of the heart and another one of the upper threshold levels corresponds to the atrial channel of the heart.

7. An implantable medical device as claimed in claim 6, wherein one of said lower threshold levels corresponds to the ventricular channel and another one of the lower threshold levels corresponds to the atrial channel.

8. An implantable medical device as claimed in claim 2, wherein said interrupt signals is comprised of a leading edge ventricular upper signal, a trailing edge ventricular upper signal, a leading edge ventricular lower signal, a trailing edge ventricular lower signal, a leading edge atrial upper signal, a trailing edge atrial upper signal, a leading edge atrial lower signal, and a trailing edge atrial lower signal.

9. An implantable medical device as claimed in claim 2, wherein said threshold means includes means for sequentially comparing said programmed threshold levels with the ECG heart signal to provide the interrupt signals.

* * * * *